(12) United States Patent
Avalle et al.

(10) Patent No.: US 8,674,105 B2
(45) Date of Patent: Mar. 18, 2014

(54) CRYSTALLINE HYDROCHLORIDE SALTS OF C-MET KINASE INHIBITORS

(75) Inventors: Paolo Avalle, Schachen (CH); Minhua Chen, Scotch Plains, NJ (US)

(73) Assignees: Merck Sharp & Dohme Limited, Hertfordshire (GB); Merck Sharp & Dohme Corp., Rahway, NJ (US)

( * ) Notice: Subject to any disclaimer, the term of this patent is extended or adjusted under 35 U.S.C. 154(b) by 60 days.

(21) Appl. No.: 13/498,605

(22) PCT Filed: Sep. 21, 2010

(86) PCT No.: PCT/US2010/049556
§ 371 (c)(1),
(2), (4) Date: Mar. 28, 2012

(87) PCT Pub. No.: WO2011/041157
PCT Pub. Date: Apr. 7, 2011

(65) Prior Publication Data
US 2012/0184744 A1    Jul. 19, 2012

Related U.S. Application Data

(60) Provisional application No. 61/247,028, filed on Sep. 30, 2009.

(51) Int. Cl.
*C07D 221/00*    (2006.01)
*A61K 31/44*    (2006.01)

(52) U.S. Cl.
USPC .......................................................... 546/93

(58) Field of Classification Search
USPC ........................................... 546/93; 514/290
See application file for complete search history.

(56) References Cited

U.S. PATENT DOCUMENTS

| | | | |
|---|---|---|---|
| 7,550,478 B2 | 6/2009 | Dinsmore et al. | |
| 8,101,603 B2 | 1/2012 | Dinsmore et al. | |
| 8,222,269 B2 * | 7/2012 | Dinsmore et al. | 514/290 |
| 2009/0203684 A1 | 8/2009 | Dinsmore et al. | |

FOREIGN PATENT DOCUMENTS

| | | |
|---|---|---|
| WO | 03084931 A1 | 10/2003 |
| WO | 2007002254 A2 | 1/2007 |
| WO | 2007002258 A2 | 1/2007 |
| WO | 2008008310 A2 | 1/2008 |
| WO | 2008067119 A2 | 6/2008 |

OTHER PUBLICATIONS

Christensen, JG et al., Cancer Research, vol. 63, (2003), pp. 7345-7355, "A selective small molecule inhibitor of cMet kinase inhibits c-Met-dependent phenotypes in Vitro and exhibits cytoreductive antitumor activity in Vivo".
Sattler, M et al., Cancer Research, vol. 63, (2003), pp. 5462-5469, "A novel small molecule Met inhibitor induces apoptosis in cells transformed by the oncogenic TPR-MET tyrosine kinase".
Christensen, JG et al., Cancer Letters, vol. 225, (2005), pp. 1-26, "c-Met as a target for human cancer and characterization of inhibitors for therapeutic intervention".
Puri, N et al., Cancer Research, vol. 67, No. 8, (2007), pp. 3529-3534, "A selective small molecule of c-Met, PHA665752, inhibits tumorigenicity and angiogenesis in mouse lung cancer xenografts".
Zou, HY et al., Cancer Research, vol. 67, No. 9, (2007), pp. 4408-4417, "An orally available small-molecule inhibitor of c-Met, PF-2341066, exhibits cytoreductive antitumor efficacy through antiproliferative and antiangiogenic mechanisms".
Martens, T et al., Clinical Cancer Research, vol. 12, No. 20, (2006), pp. 6144-6152, "A novel one-armed anti-c-Met antibody inhibits glioblastoma growth in vivo".
Northrup, A et al., "Discovery of MK-8033, a highly specific c-Met/Ron dual inhibitor for the treatment of cancer", Poster #759, 101st American Association for Cancer Research Annual Meeting, Washington, DC, Apr. 17-21, 2010.
Baselga, J et al., Science, vol. 312, (2006), pp. 1175-1178, "Targeting tyrosine kinases in cancer: the second wave".
Cosmoglio, PM et al., Nature Reviews Drug Discovery, vol. 7, (2008), pp. 504-516, "Drug development of MET inhibitors: targeting oncogene addiction and expedience".
NCT00559182 on Nov. 15, 2007 available at: http://clinicaltrials.gov/archive/NCT00559182/2007_11_15.
NCT00559182 on Aug. 14, 2008 available at: http://clinicaltrials.gov/archive/NCT00559182/2008_08_14.
NCT00559182 on Aug. 31, 2009 available at: http://clinicaltrials.gov/archive/NCT00559182/2009_08_31.
Bhardwaj, Vet al., Journal of Thoracic Oncology, vol. 7, No. 8, (2012), pp. 1211-1217, "C-Met inhibitor MK-8003 radiosensitizes c-Met-expressing non-small-cell-lung cancer cells with radiation-induced c-Met-expression".

* cited by examiner

*Primary Examiner* — John Mabry
(74) *Attorney, Agent, or Firm* — Richard S. Parr; Laura M. Ginkel

(57) ABSTRACT

The instant invention relates to crystalline forms of Compound A, an inhibitor of c-MET kinase. Specifically, the instant invention relates to hydrochloride salts of Compound A.

10 Claims, 11 Drawing Sheets

CRYSTALLINE HYDROCHLORIDE SALTS OF C-MET KINASE INHIBITORS

BACKGROUND OF THE INVENTION

This invention relates to crystalline-forms of c-Met kinase inhibitors. A variety of c-Met kinase inhibitors have been disclosed for the treatment of various disorders related to c-Met kinase functioning, including the treatment of cellular proliferative disorders. Such disorders include, but are not limited to, cancer, hyperplasias, restenosis, cardiac hypertrophy immune disorders and inflammation. Representative examples of c-Met kinase inhibitors include those disclosed International Publication WO2008/008310, which published on Jan. 17, 2008, to Merck & Co., Inc., which is hereby incorporated by reference in its entirety.

SUMMARY OF THE INVENTION

The instant invention relates to crystalline forms of Compound A, an inhibitor of c-MET kinase. Specifically, the instant invention relates to hydrochloride salts of Compound A.

DETAILED DESCRIPTION OF THE INVENTION

The instant invention relates to crystalline forms of Compound A, an inhibitor of c-MET kinase. Compound A is also known as 1-[3-(1-Methyl-1H-pyrazol-4-yl)-5-oxo-5H-benzo[4,5]cyclohepta[1,2-b]pyridin-7-yl]-N-(pyridin2-ylmethyl)methanesulfonamide,

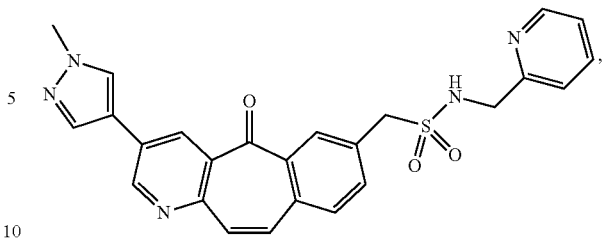

which can be prepared by procedures described in: International Publication WO2008/008310, which published on Jan. 17, 2008, to Merck & Co., Inc., which is hereby incorporated by reference in its entirety.

Specifically, the instant invention relates to hydrochloride salts of Compound A. There are three known crystalline forms for the mono-HCl salt: mono-HCl salt anhydrate Form I, mono-HCl salt hydrate and mono-HCl salt anhydrate Form II.

Additionally, there are three known crystalline phases for the 1.6-HCl salt: the 1.6-HCl salt DMF solvate, the 1.6-HCl salt hydrate and the 1.6-HCl salt anhydrate. Chloride titration of several pure 1.6-HCl salt hydrate samples have shown approximately 1.6 equivalence of HCl, suggesting 1.6-HCl salt hydrate is likely a 1.6-HCl salt.

X-ray powder diffraction studies are widely used to characterize molecular structures, crystallinity, and polymorphism. The X-ray powder diffraction patterns of the crystalline HCl salts of the present invention were generated on a Philips Analytical X'Pert PRO X-ray Diffraction System with PW3040/60 console. A PW3373/00 ceramic Cu LEF X-ray tube K-Alpha radiation was used as the source.

Mono-HCl Salt Anhydrate Form I

Figure 1:
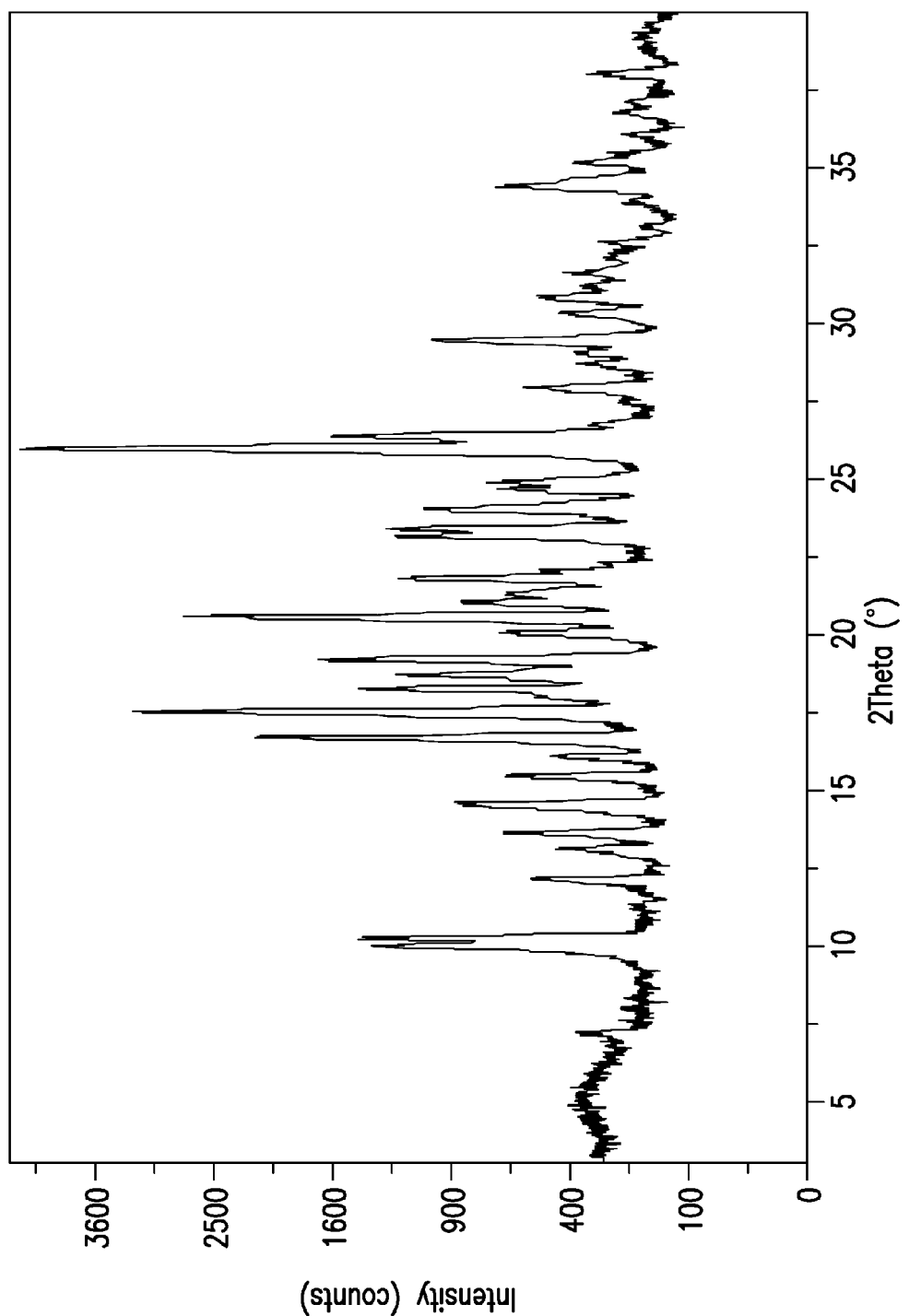
FIG. 1 is the X-ray diffraction pattern of the crystalline mono-HCl salt anhydrate Form I of Compound A.

The X-ray diffraction pattern for the crystalline mono-HCl salt anhydrate Form I of Compound A is shown in FIG. 1. The crystalline mono-HCl salt anhydrate Form I of Compound A, also known as "Form I," "mono-HCl salt anhydrate Form I" or "mono-HCl salt anhydrate Form I of Compound A," exhibits characteristic reflections corresponding to d-spacings of 5.30, 5.05, and 4.30 angstroms. The crystalline mono-HCl salt anhydrate Form I of Compound A, is further characterized by reflections corresponding to d-spacings of 7.28, 5.72, and 4.61 angstroms. The crystalline mono-HCl salt anhydrate Form I of Compound A is even further characterized by reflections corresponding to d-spacings of 6.48, 4.41, and 3.42 angstroms.

Form I was found to be physically stable after stored under room temperature/53% relative humidity, room temperature/85% relative humidity or 40° C./75% relative humidity for 5 months.

In addition to the X-ray powder diffraction patterns described above, the mono-HCl salt anhydrate Form I of Compound A is further characterized by solid-state carbon-13 nuclear magnetic resonance (NMR) spectra. The solid-state carbon-13 NMR spectra are obtained on a Bruker DSX 500WB NMR system using a Bruker 4 mm. H/X/Y CPMAS probe. The carbon-13-NMR spectra utilizes proton/carbon-13 cross-polarization magic-angle spinning with variable-amplitude cross polarization, and TPPM decoupling at 80 kHz. The samples are spun at 10.0 kHz, and a total of 512 scans are collected with a recycle delay of 90 seconds. A line broadening of 10 Hz is applied to the spectra before FT is performed. Chemical shifts are reported on the TMS scale using the carbonyl carbon of glycine (176.70 p.p.m.) as a secondary reference.

Figure 2:
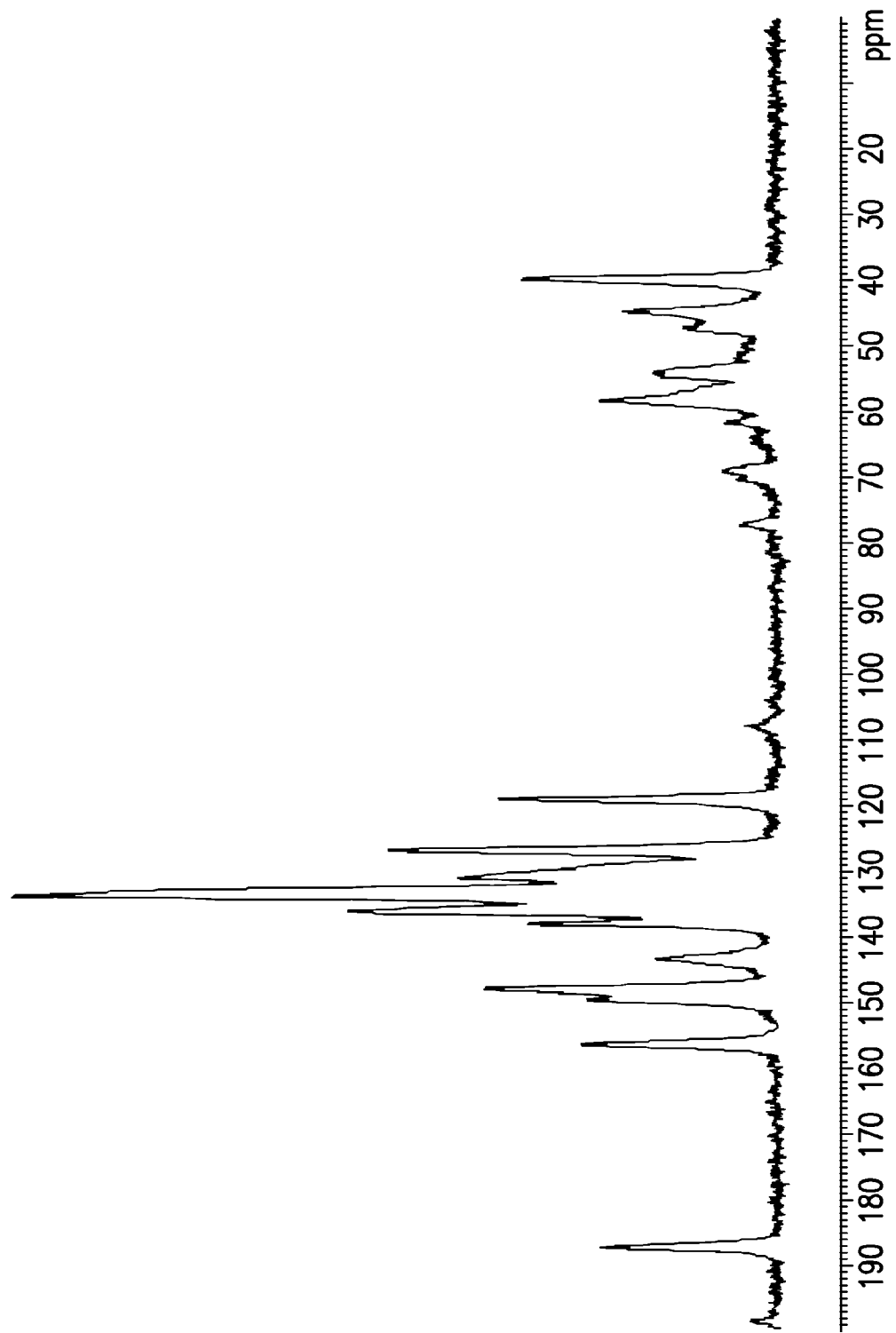
FIG. 2 is a carbon-13 cross-polarization magic-angle spinning (CPMAS) nuclear magnetic resonance (NMR) spectrum of the crystalline mono-HCl salt anhydrate Form I of Compound A.

The solid-state carbon-13 CPMAS NMR spectrum for the mono-HCl salt anhydrate Form I of Compound A is shown in FIG. 2. Form I is characterized by a solid-state carbon-13 CPMAS nuclear magnetic resonance spectrum showing signals at 133.6, 136.0 and 126.7 p.p.m. The spectrum is further characterized by signals at 131.0, 147.9 and 118.9 p.p.m.

DSC data are acquired using TA Instruments DSC 2910 or equivalent instrumentation. Between 1 and 7 mg sample are weighed into an open pan. This pan is then crimped and placed at the sample position in the calorimeter cell. An empty crimped pan is placed at the reference position. The calorimeter cell is closed and a flow of nitrogen was passed through the cell. The heating program is set to heat the sample at a heating rate of 10° C./min to a temperature of approximately 280° C. The heating program is started. When the run is completed, the data are analyzed using the DSC analysis program contained in the system software. The melting endotherm is integrated between baseline temperature points that are above and below the temperature range over which the endotherm is observed. The data reported are the onset temperature, peak temperature and enthalpy.

Figure 3:
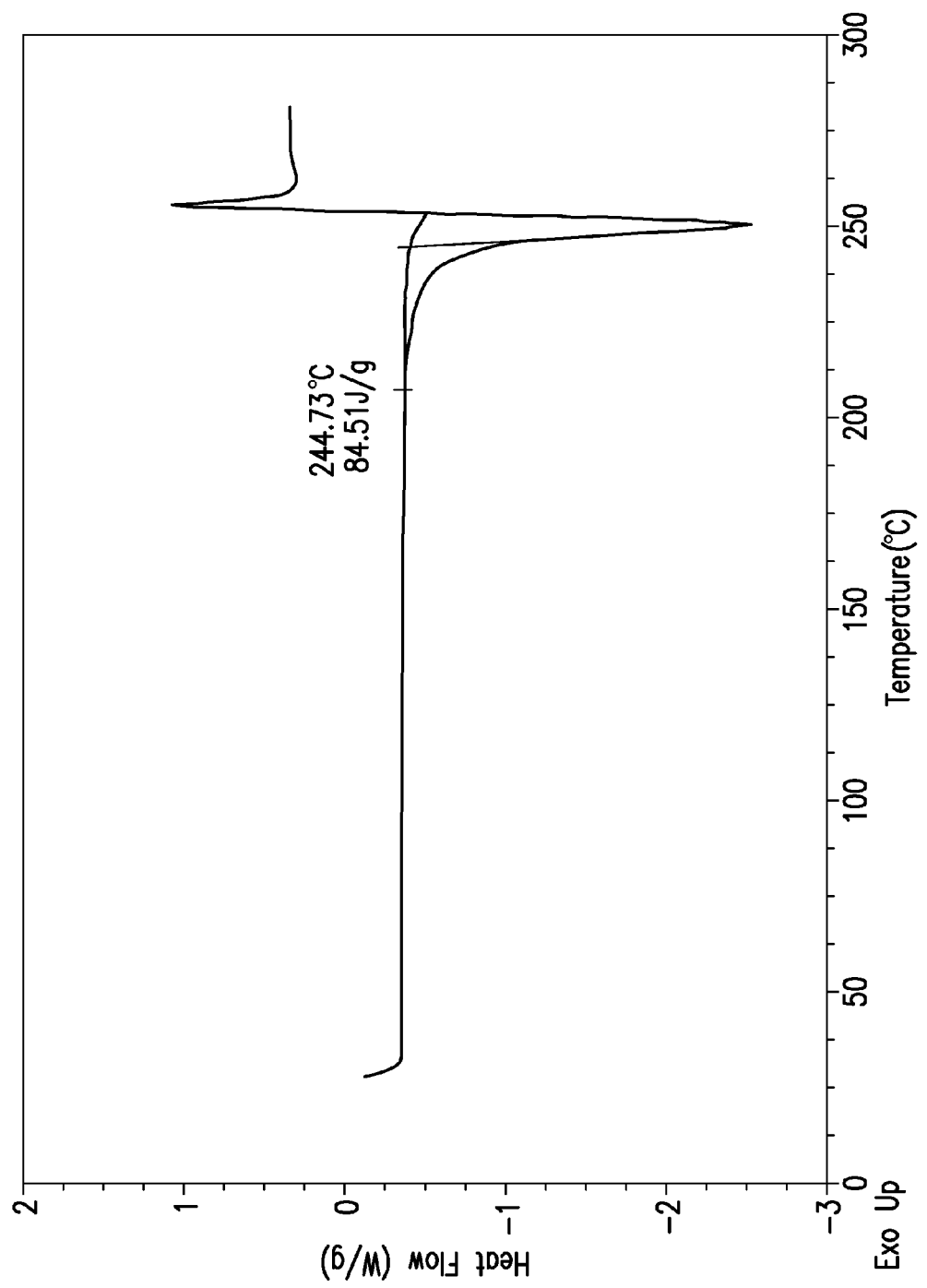
FIG. 3 is a typical DSC curve of the crystalline mono-HCl salt anhydrate Form I of Compound A.

The differential calorimetry scan for the mono-HCl salt anhydrate Form I of Compound A is shown in FIG. 3. The mono-HCl salt anhydrate Form I of Compound A exhibited an endotherm due to melting and degradation with an onset temperature of 244.7° C., a peak temperature of 250.6° C., and an enthalpy change of 84.5 J/g.

Thermogravimetric (TG) data are acquired using a Perkin Elmer model TGA 7 or equivalent instrumentation. Experiments are performed under a flow of nitrogen and using a heating rate of 10° C./min to a maximum temperature of approximately 280° C. After automatically taring the balance, 5 to 20 mg of sample is added to the platinum pan, the furnace is raised, and the heating program started. Weight/temperature data are collected automatically by the instrument. Analysis of the results is carried out by selecting the Delta Y function within the instrument software and choosing the temperatures between which the weight loss is to be calculated. Weight losses are reported up to the onset of decomposition/evaporation.

Figure 4:
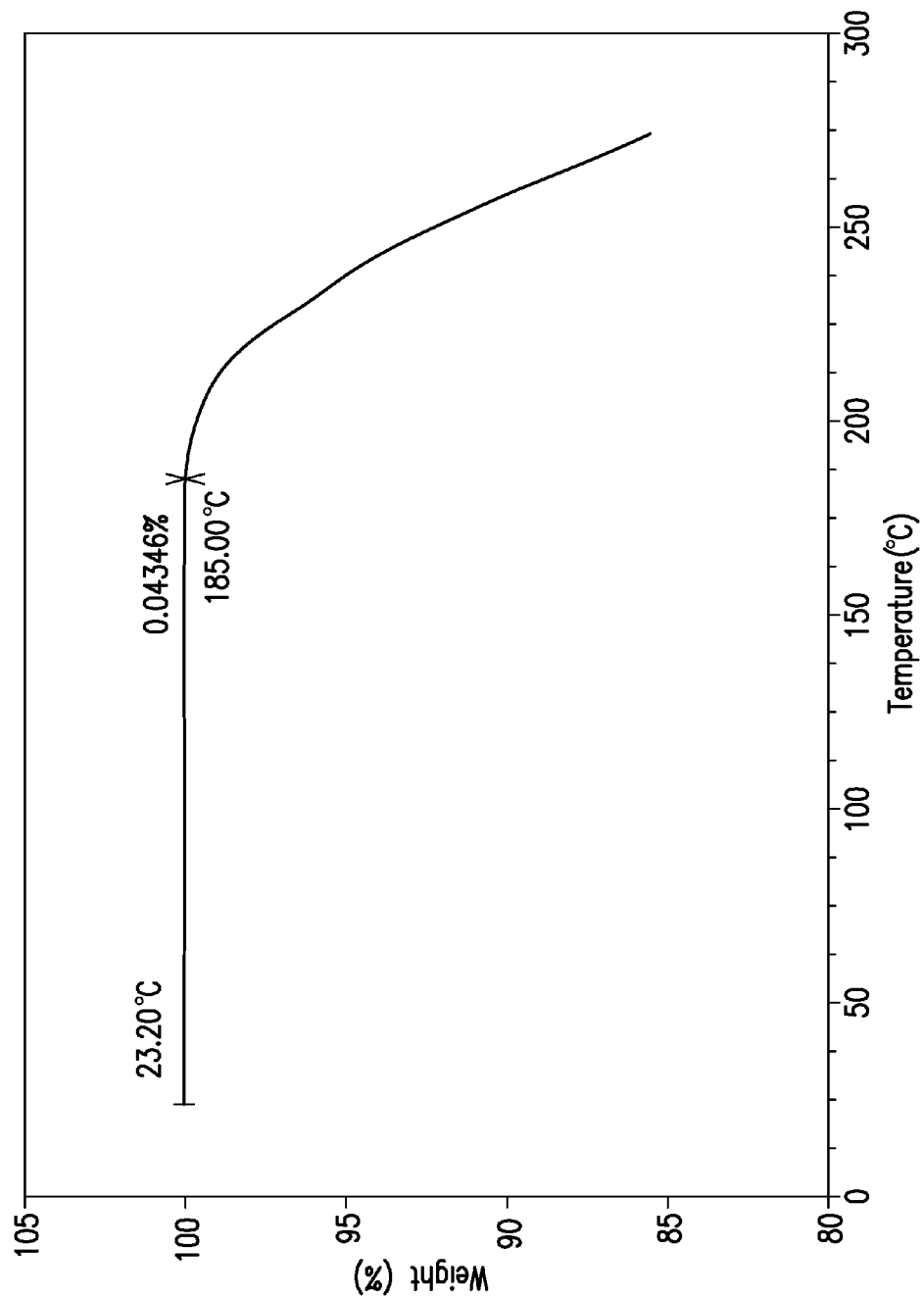
FIG. 4 is a typical thermogravimetric (TG) curve of the crystalline mono-HCl salt anhydrate Form I of Compound A.

A characteristic thermogravimetric analysis (TGA) curve for the mono-HCl salt anhydrate Form I of Compound A is shown in FIG. 4. TGA indicated a weight loss of about 0.04% from ambient temperature to about 185° C.

1.6-HCl Salt Hydrate

Figure 5:
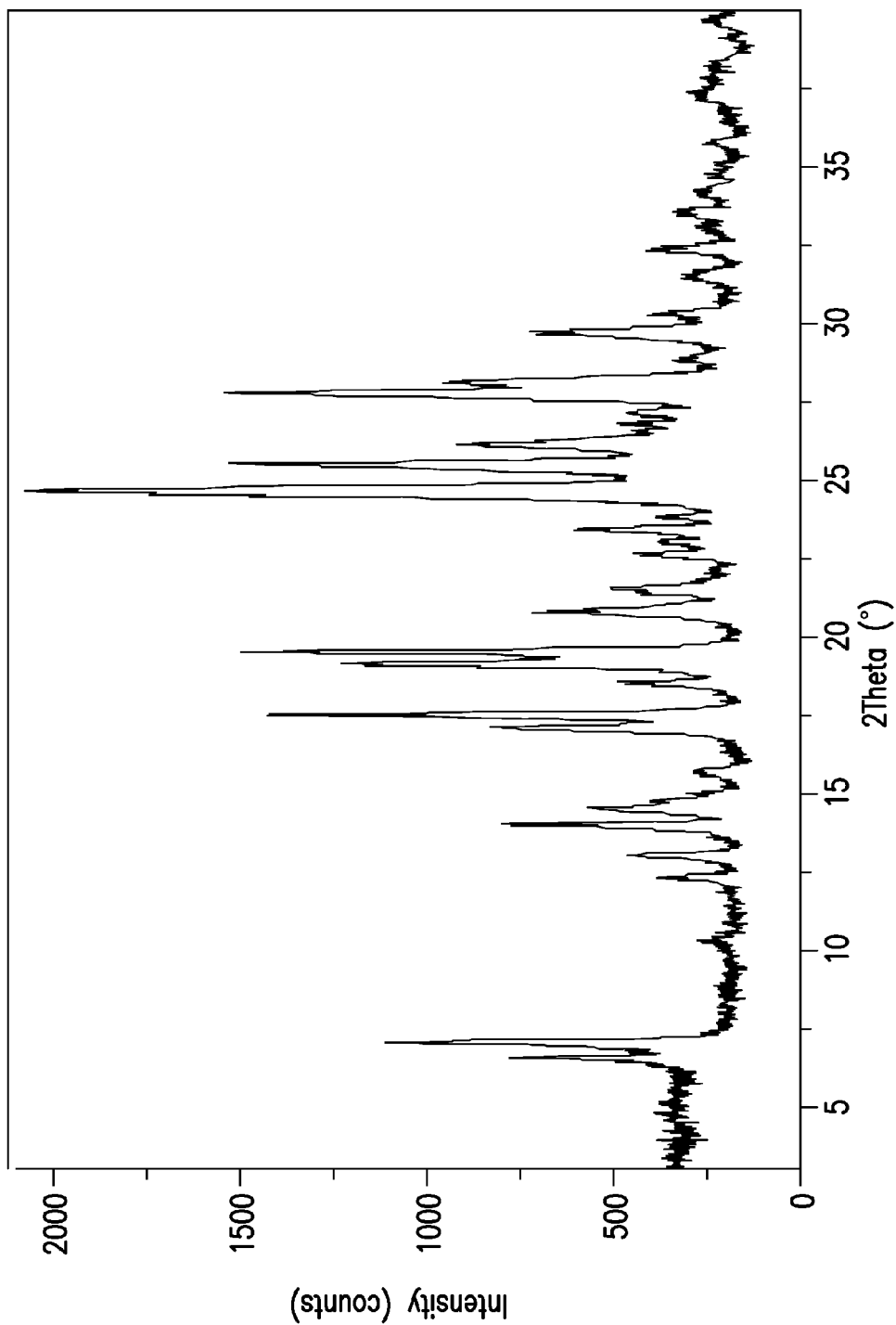
FIG. 5 is the X-ray diffraction pattern of the crystalline 1.6-HCl salt hydrate of Compound A.

The X-ray diffraction pattern for the crystalline 1.6-HCl salt hydrate of Compound A is shown in FIG. 5. The crystalline 1.6-HCl salt hydrate of Compound A, also known as "1.6-HCl salt hydrate of Compound A," "1.6-HCl salt hydrate," or "channel monohydrate" exhibited characteristic reflections corresponding to d-spacings of 12.58, 6.31, and 5.18 angstroms. The 1.6-HCl salt hydrate of Compound A is further characterized by reflections corresponding to d-spacings of 5.05, 4.63, and 4.54 angstroms. The 1.6-HCl salt hydrate is even further characterized by reflections corresponding to d-spacings of 3.48, 3.20, and 3.00 angstroms.

Figure 6:
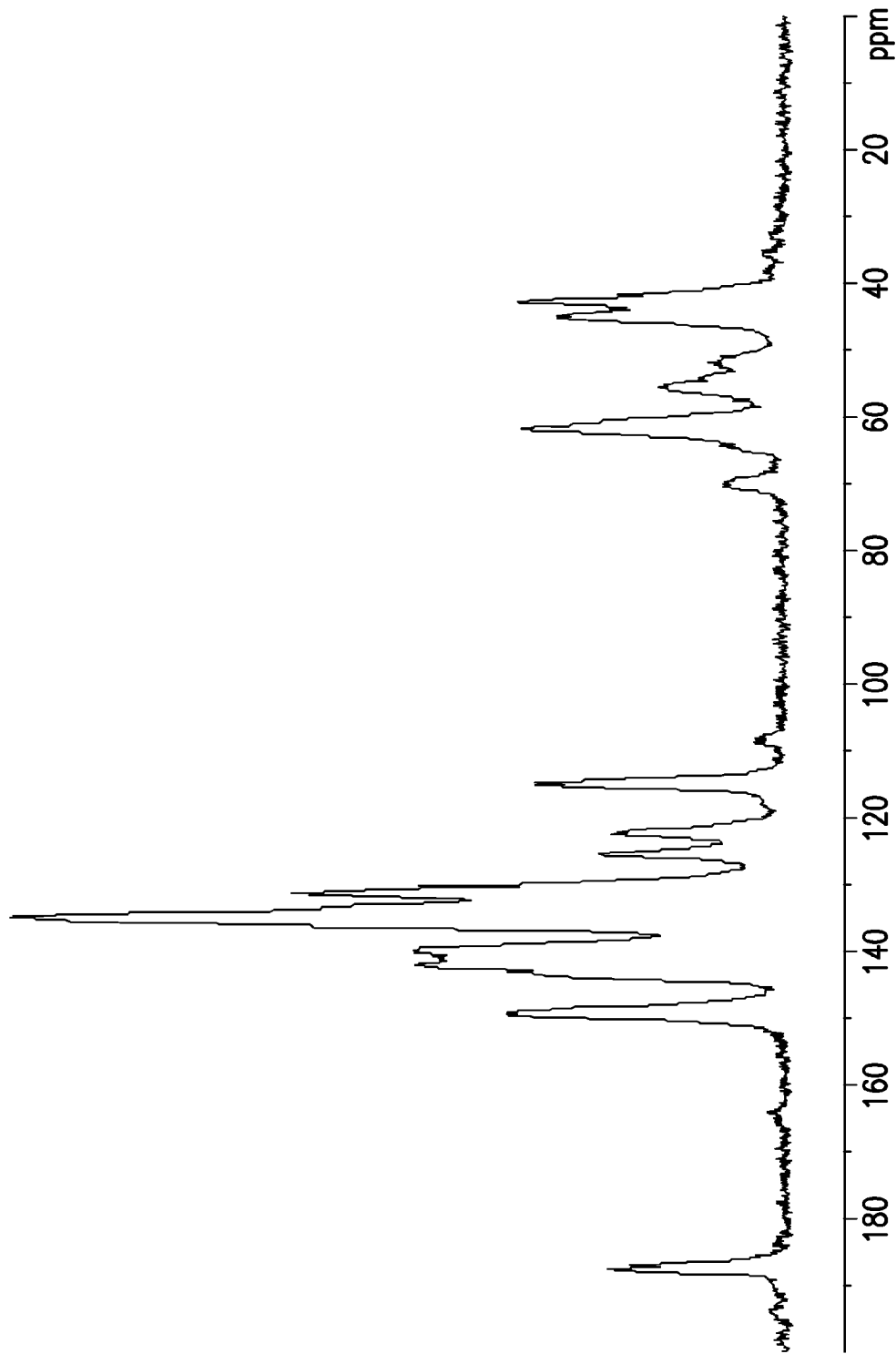
FIG. 6 is a carbon-13 cross-polarization magic-angle spinning (CPMAS) nuclear magnetic resonance (NMR) spectrum of the crystalline 1.6-HCl salt hydrate of Compound A.

The solid-state carbon-13 CPMAS NMR spectrum for the 1.6-HCl salt hydrate of Compound A is shown in FIG. 6.

Figure 7:
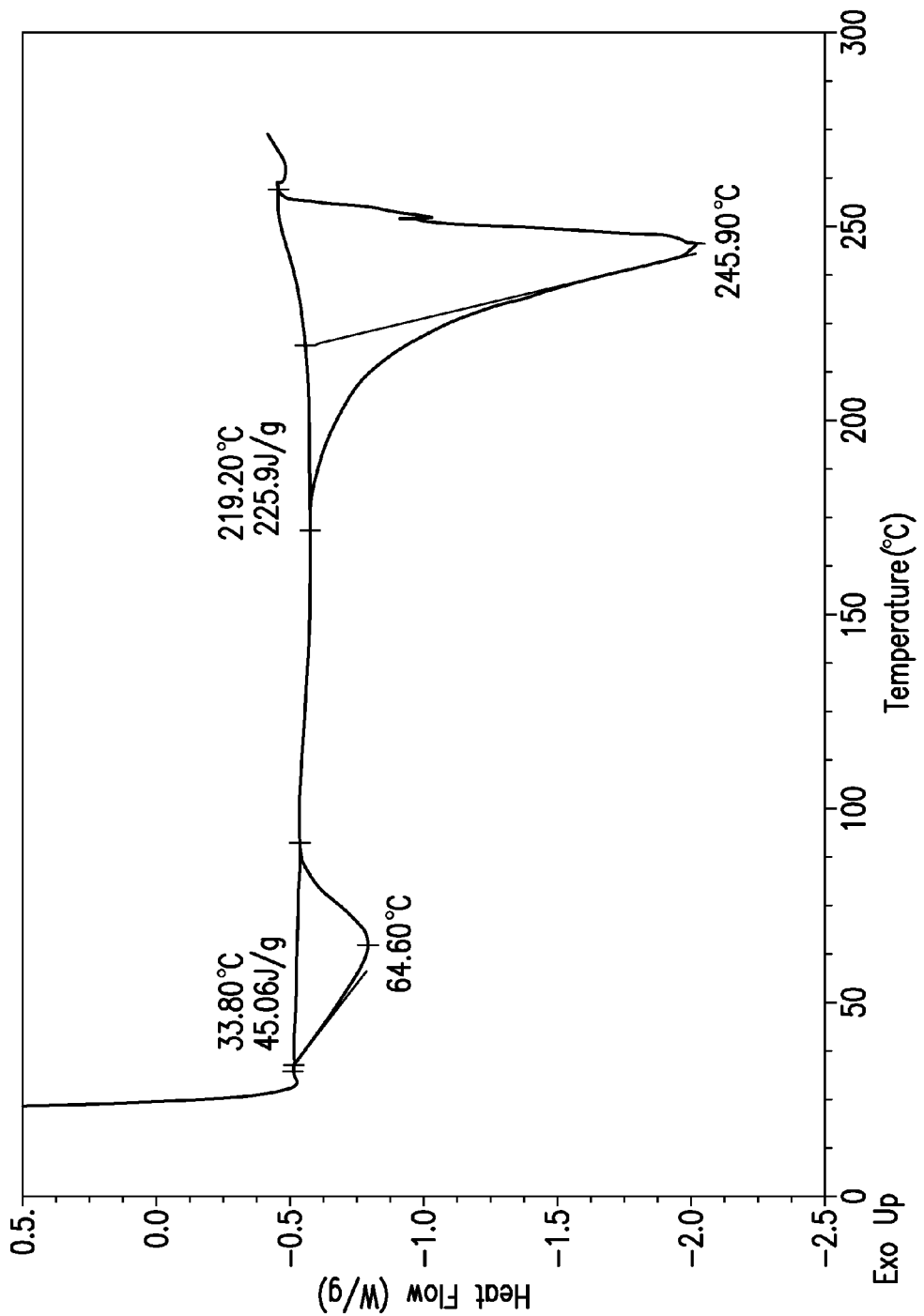
FIG. 7 is a typical DSC curve of the crystalline 1.6-HCl salt hydrate of Compound A.

The differential calorimetry scan for the 1.6-HCl salt hydrate of Compound A is shown in FIG. 7. The 1.6-HCl salt hydrate exhibited an endotherm due to dehydration with an onset temperature of 45.1° C., a peak temperature of 64.6° C., and an enthalpy change of 33.8 J/g. The 1.6-HCl salt hydrate exhibited a second endotherm due to melting and degradation with an onset temperature of 219.2° C., a peak temperature of 245.9° C., and an enthalpy change of 225.9 J/g.

Upon slurry in Acetone:$H_2O$ or other cosolvent systems with high water activity, 1.6-HCl salt hydrate will convert to the mono-HCl salt hydrate. The 1.6-HCl salt hydrate can be prepared by slurrying Form I in pure DMF solvent or DMF:IPA:H2O cosolvent with low water activity at 55° C. Furthermore, the 1.6-HCl salt hydrate can be prepared by slurrying Form I in pure DMF solvent or DMF:IPA:H2O cosolvent with excess amount of free HCl. Lower water activity and higher molar ratio of HCl to compound in the system will favor the conversion of Form I to the 1.6-HCl salt hydrate.

Mono-HCl Salt Hydrate

Figure 8:
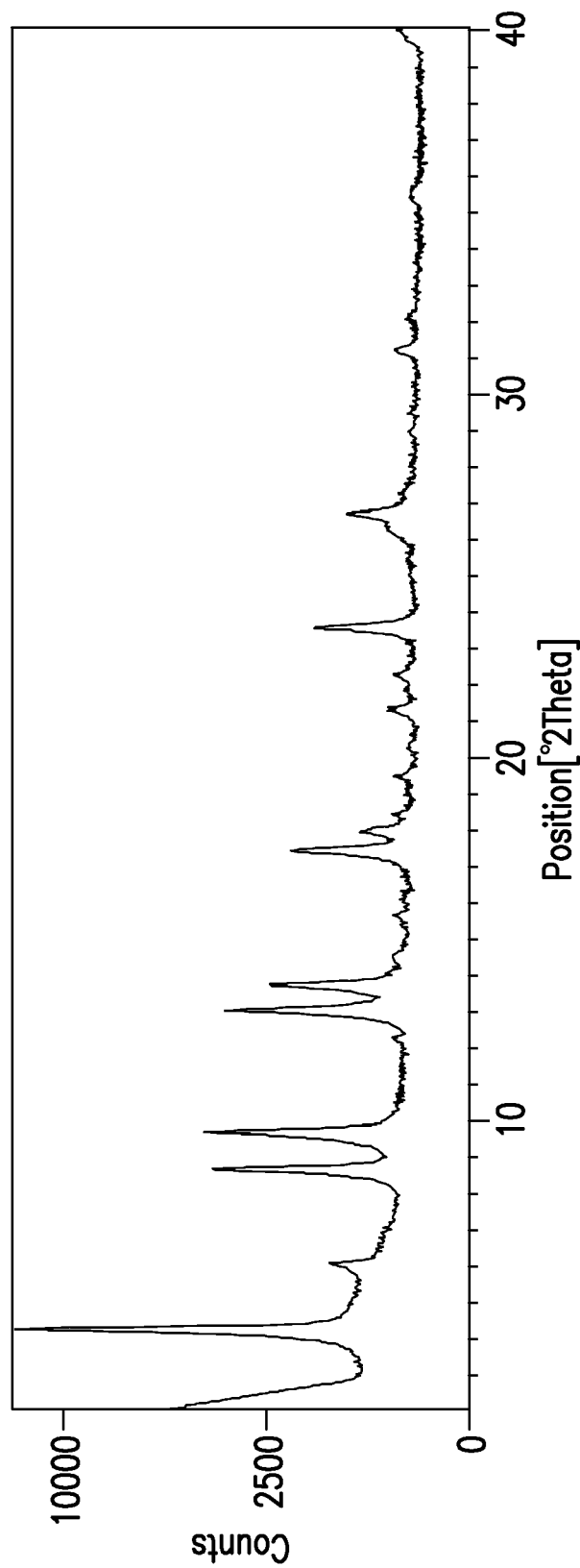
FIG. 8 is the X-ray diffraction pattern of the crystalline mono-HCl salt hydrate of Compound A.

The X-ray diffraction pattern for the crystalline mono-HCl salt hydrate of Compound A is shown in FIG. 8. The crystalline mono-HCl salt hydrate of Compound A, also known as "mono-HCl hydrate," or "mono-HCl salt hydrate of Compound A" exhibits characteristic reflections corresponding to d-spacings of 20.60, 10.20, and 9.14 angstroms. The mono-HCl salt hydrate of Compound A is further characterized by reflections corresponding to d-spacings of 6.78, 6.44, and 5.08 angstroms. The mono-HCl salt hydrate of Compound A is even further characterized by reflections corresponding to d-spacings of 4.93, 3.98, and 3.34 angstroms.

With respect to mono-HCl salt, the crystalline mono-HCl salt hydrate is thermodynamically more stable than the mono-HCl salt anydrate Form I above transition water activity of ~0.57-0.60 at room temperature or 40° C. This transition water activity was determined based on slurry experiment in Acetone:$H_2O$, DMF:$H_2O$ and THF:$H_2O$ co-solvent. However, solid conversion of Form I to the mono-HCl salt hydrate has not been observed. Form I was found to be physically stable after stored under room temperature/53% relative humidity, room temperature/85% relative humidity or 40° C./75% relative humidity for 5 months. Crystalline mono-HCl salt hydrate dehydrates and converts to mono-HCl salt anhydrate Form II when exposed to low relative humidity or heated at high temperature.

Mono-HCl Salt Anhydrate Form II

Figure 9:
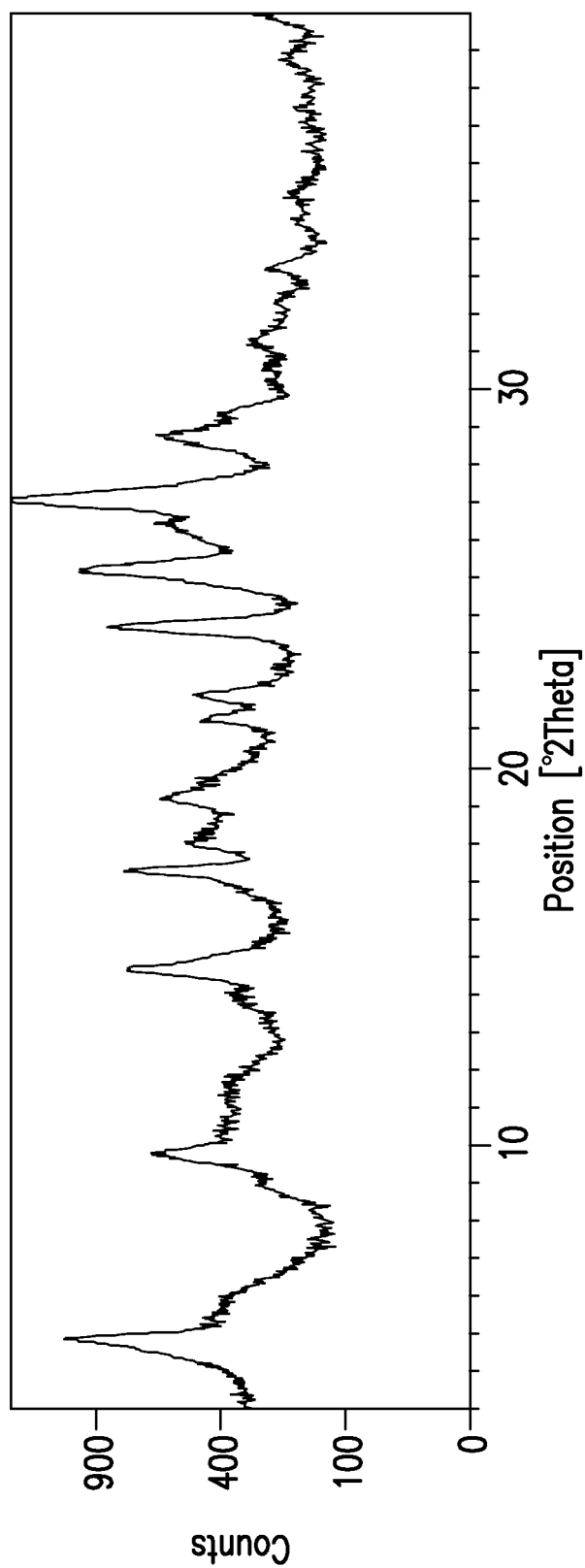
FIG. 9 is the X-ray diffraction pattern of the crystalline mono-HCl salt anhydrite Form II of Compound A.

The X-ray diffraction pattern for the crystalline mono-HCl salt anhydrate Form II of Compound A is shown in FIG. 9. The crystalline mono-HCl salt anhydrate Form II of Compound A, also known as "Form II" "mono-HO salt anhydrate Form II of Compound A" or "mono-HCl salt anhydrate Form II," exhibits characteristic reflections corresponding to d-spacings of 18.25, 9.10, and 6.03 angstroms. The mono-HCl salt anhydrate Form II of Compound A is further characterized by reflections corresponding to d-spacings of 5.13, 4.61, and 4.17 angstroms. The mono-HCl salt anhydrate Form II of Compound A is even further characterized by reflections corresponding to d-spacings of 3.75, 3.53, and 3.29 angstroms.

Crystalline mono-HCl salt anhydrate Form II displays low crystallinity by XRPD. It rehydrates and converts back to the mono-HCl salt hydrate when exposed to higher than 75% relative humidity at room temperature. The mono-HCl salt anhydrate Form II can also convert to crystalline mono-HCl salt anhydrate Form I when slurried in Acetone:$H_2O$ co-solvent or other co-solvent systems with water activity below 0.57-0.60.

1.6 HCl Salt DMF Solvate

Figure 11:
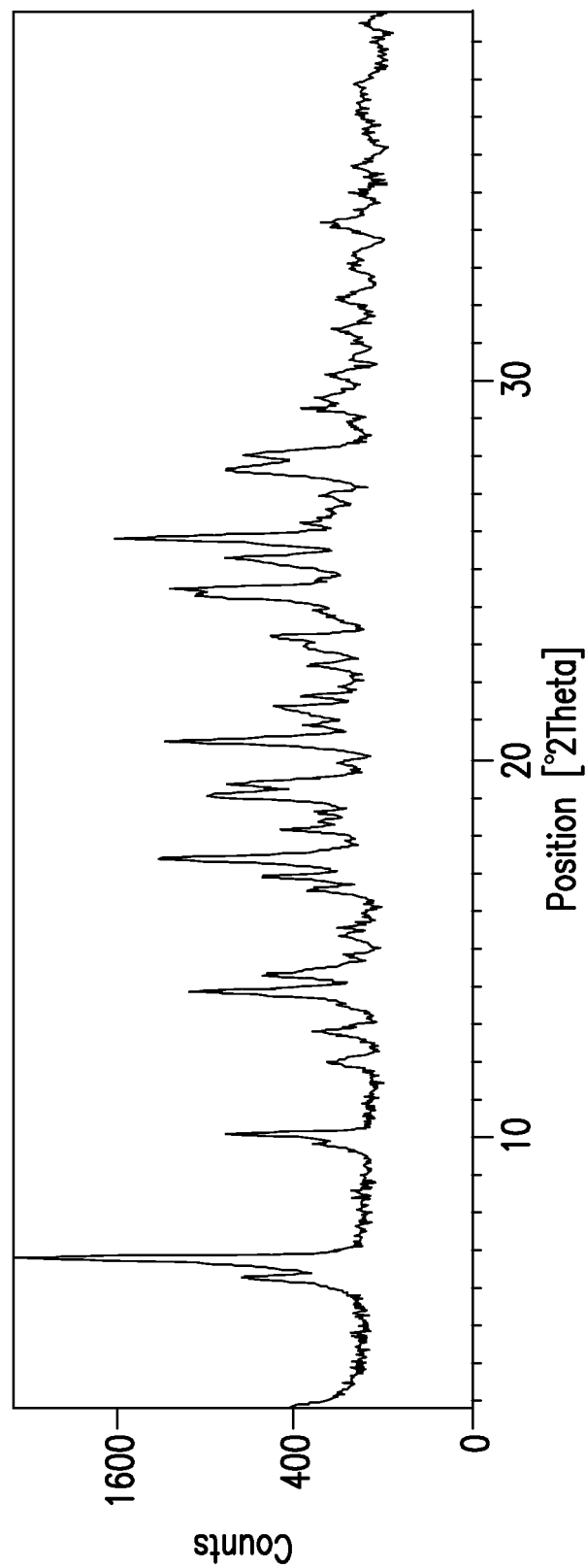
FIG. 11 is the X-ray diffraction pattern of the crystalline 1.6-HCl salt DMF solvate of Compound A.

The X-ray diffraction pattern for the crystalline 1.6-HCl salt DMF solvate of Compound A is shown in FIG. 11. The crystalline 1.6-HCl salt DMF solvate of Compound A, also known as "DMF solvate," "channel DMF solvate of 1.6-HCl complex," "1.6-HCl salt DMF solvate of Compound A," or "1.6-HCl DMF solvate", exhibited characteristic reflections corresponding to d-spacings of 12.98, 8.76, and 6.39 angstroms. The 1.6-HCl salt DMF solvate of Compound A is further characterized by reflections corresponding to d-spacings of 6.19, 5.10, and 4.34 angstroms. The 1.6-HCl salt DMF solvate of Compound A is even further characterized by reflections corresponding to d-spacings of 3.51, 3.44, and 3.04 angstroms.

The mono-HCl salt anhydrate Form I of Compound A can convert to the 1.6-HCl DMF solvate upon slurry in DMF:H$_2$O solvent system, dependent on the HCl equivalence, water activity, DMF activity and temperature of the whole system. In general, higher equivalence of HCl, higher DMF activity and lower water activity will favor the formation of 1.6-HCl DMF solvate. DMF solvate is a transient channel solvate and converts to the 1.6-HCl salt anhydrate upon desolation at low relative humidity.

1.6-HCl Salt Anhydrate

Figure 10:
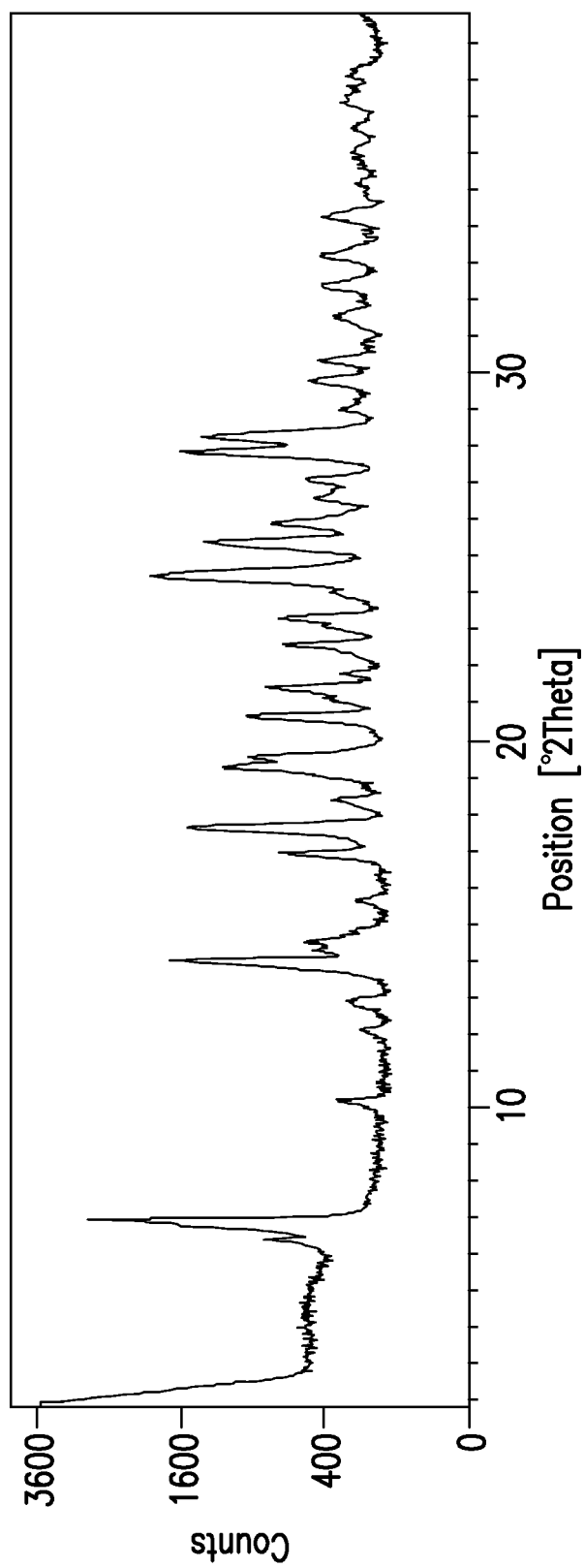
FIG. 10 is the X-ray diffraction pattern of the crystalline 1.6-HCl salt anhydrate of Compound A.

The X-ray diffraction pattern for the crystalline 1.6-HCl salt anhydrate of Compound A is shown in FIG. 10. The crystalline 1.6-HCl salt anhydrate of Compound A, also known as "1.6-HCl salt anhydrate of Compound A" or "1.6-HCl salt anhydrate," exhibited characteristic reflections corresponding to d-spacings of 12.79, 6.33, and 5.23 angstroms. The 1.6-HCl salt anhydrate of Compound A is further characterized by reflections corresponding to d-spacings of 5.03, 4.30, and 4.14 angstroms. The 1.6-HCl salt anhydrate of Compound A is even further characterized by reflections corresponding to d-spacings of 3.93, 3.63, and 3.50 angstroms.

The 1.6-HCl salt anhydrate converts to the 1.6-HCl salt hydrate upon exposure to 10-95% relative humidity at room temperature. The DMF solvate displays a very similar XRPD pattern to the 1.6-HCl salt anhydrate.

The compounds of the present invention can be prepared according to the following specific examples. The compounds illustrated in the examples are not, however, to be construed as forming the only genus that is considered as the invention. Those skilled in the art will readily understand that known variations of the conditions and processes of the following preparative procedures can be used to prepare these compounds. All temperatures are degrees Celsius unless otherwise noted.

Example 1

Preparation of Mono-HCl Salt Anhydrate Form I of Compound A

Preparation

To prepare the HCl, dilute concentrated aqueous HCl (37 wt %) to 3.0 M with IPA. To prepare the solution (wash and media milling solution), prepare 14.6 wt % IPA in DMF. To prepare the media milled seed prep, media mill 15.0 wt % API in IPA/DMF solvent. IPA/DMF is 14.6 wt % IPA in DMF.

Batch

To prepare the mono-HCl salt anhydrate Form I of Compound A, dissolve 1.00 g of Compound A freebase monohydrate in 7.0 mL (6.65 g) DMF at 55° C. Next, charge 0.05 eq of HCl. Then, charge 0.25 wt % media-milled seed (0.00625 mg of API). The solubility of Compound A HCl seed in 14.6 wt % IPA in DMF is <2 mg/mL. Age seed bed for 1 hr. Next, charge 0.92 eq of HCl over 8 hrs (linear charge rate) holding batch at 55. No dispersion is required. Total HCl charge is 0.97 eq. Cool the batch from 55° C. to 22° C. over 1 hr. Hold batch at 22° C. for one hour, then filter.

Wash cake with 3 mL of 14.6 wt % IPA in DMF. Slurry wash cake with 3 mL IPA (to remove DMF). Slurry wash cake with 3 mL IPA (to remove DMF). Displacement wash cake with 3 mL IPA. Dry under vacuum at 60° C.

Example 2

Preparation of Mono-HCl Salt Hydrate of Compound A

The mono-HCl salt hydrate of Compound A can be prepared by slurrying mono-HCl salt anhydrite Form I in Acetone:H$_2$O, THF:H$_2$O, DMF:H$_2$O or other organic solvent-water co-solvent system with water activity higher than ~457-0.60 at RT or 40° C.

Example 3

Preparation of Mono-HCl Salt Anhydrate Form II of Compound A

The mono-HCl salt anhydrite Form II of Compound A can be prepared by dehydrating the mono-HCl salt hydrate of Compound A at RT with low RH or at high temperature.

Example 4

Preparation of 1.6-HCl Salt Hydrate of Compound A

The 1.6-110 salt hydrate can be prepared by charging 4.9962 g of Compound A monohydrate to a visually clean vessel. Next, 35 mL DMF added. The vessel is connected to a bath pre-heated to 55° C.

1.687 mL of conc HCl (12.1 M; 2 equiv.) is charged to the vessel; the batch remained yellow solution for about 1 minute, then formed thick yellow slurry. The slurry was filtered & DMF wet solids washed 5× with IPA.

Bath is set to 22° C. After 35 minutes, the batch is filtered on a glass fit filter. Cake slurry washed 2× with 15 mL IPA then displacement washed once with 15 mL IPA. The filter is left on vacuum under ambient atmosphere for 20 min then placed in 40° C. vac oven to dry overnight.

Example 5

Preparation of 1.6-HCl Salt Anhydrate of Compound A

The 1.6-HCl salt anhydrate can be prepared by dehydrating the 1.6-HCl salt hydrate at room temperature with low relative humidity or at high temperature.

Example 6

Preparation of 1.6-HCl Salt DMF Solvate of Compound A

The 1.6-HCl salt DMF solvate can be prepared by slurrying the 1.6-HCl salt hydrate in DMF solvent.

What is claimed is:
1. Crystalline 1-[3-(1-Methyl-1H-pyrazol-4-yl)-5-oxo-5H-benzo[4,5]cyclohepta[1,2-b]pyridin-7-yl]-N-(pyridin-2-ylmethyl)methanesulfonamide hydrochloride salt.
2. A novel crystalline mono-HCl salt anhydrate Form I of 1-[3-Methyl-1H-pyrazol-4-yl)-5-oxo-5H-benzo[4,5]cyclohepta[1,2-b]pyridin-7-yl]-N-(pyridin-2-ylmethyl)methanesulfonamide which is characterized by an x-ray powder dif- fraction pattern, collected using copper Kα radiation, corresponding to d-spacings of 5.30, 5.05 and 4.30 angstroms.

3. The novel crystalline mono-HCl salt anhydrate of form I of 1-[3-Methyl-1H-pyrazol-4-yl)-5-oxo-5H-benzo[4,5]cyclohepta[1,2-]pyridin-7-yl]-N-(pyridin-2-ylmethyl)methanesulfonamide of claim 1 which is further characterized by reflections corresponding to d-spacings of 7.28, 5.72, and 4.61 angstroms.

4. The novel crystalline mono HCl salt anhydrate of form I of 1-[3-(1-Methyl-1H-pyrazol-4-yl)-5-oxo-5H-benzo[4,5]cyclohepta[1,2-b]pyridin-7-yl]-N-(pyridin-2-ylmethyl)methanesulfonamide of claim 1 which is further characterized by reflections corresponding to d-spacings of 6.48, 4.41, and 3.42 angstroms.

5. The novel crystalline mono-HCl salt anhydrate Form I of 1-[3-(1-Methyl-1H-pyrazol-4-yl)-5-oxo-5H-benzo[4,5]cyclohepta[1,2-b]pyridin-7-yl]-N-(pyridin-2-ylmethyl)methanesulfonamide of claim 2 which is characterized by a solid-state carbon-13 CPMAS nuclear magnetic resonance spectrum showing signals at 133.6, 136.0 and 126.7 p.p.m.

6. The novel crystalline mono-HCl salt anhydrate Form I of 1-[3-(1-Methyl-1H-pyrazol-4-yl)-5-oxo-5H-benzo[4,5]cyclohepta[1,2-b]pyridin-7-yl]-N-(pyridin-2-ylmethyl)methanesulfonamide of claim 5 which is further characterized by signals at 131.0, 147.9 and 118.9 p.p.m.

7. The novel crystalline mono-HCl salt anhydrate Form I of 1-[3-(1-Methyl-1H-pyrazol-4-yl)-5-oxo-5H-benzo[4,5]cyclohepta[1,2-b]pyridin-7-yl]-N-(pyridin-2-ylmethyl)methanesulfonamide of claim 6 which is characterized by melting onset at 244.7° C.

8. A novel crystalline 1.6-HCl salt hydrate of 1-[3-(1-Methyl-1H-pyrazol-4-yl)-5-oxo-5H-benzo[4,5]cyclohepta[1,2-b]pyridin-7-yl]-N-(pyridin-2-ylmethyl)methanesulfonamide which is characterized by an x-ray powder diffraction pattern, collected using copper Kα radiation, corresponding to d-spacings of 12.58, 6.31 and 5.18 angstroms.

9. The novel crystalline 1.6-HCl salt hydrate of 1-[3-(1-Methyl-1H-pyrazol-4-yl)-5-oxo-5H-benzo[4,5]cyclohepta[1,2-b]pyridin-7-yl]-N-(pyridin-2-ylmethyl)methanesulfonamide of claim 8 which is further characterized by d-spacings of 5.05, 4.63 and 4.54 angstroms.

10. The novel crystalline 1.6-HCl salt hydrate of 1-[3-Methyl-1H-pyrazol-4-yl)-5-oxo-5H-benzo[4,5]cyclohepta[1,2-b]pyridin-7-yl]-N-(pyridin-2-ylmethyl)methanesulfonamide of claim 9 which is characterized by melting onset at 219.2° C.

* * * * *